(12) United States Patent
Inan et al.

(10) Patent No.: US 12,245,874 B2
(45) Date of Patent: Mar. 11, 2025

(54) GLOVE-BASED FORM FACTOR FOR BIO-ACOUSTICAL SENSING

(71) Applicant: Georgia Tech Research Corporation, Atlanta, GA (US)

(72) Inventors: Omer T. Inan, Atlanta, GA (US); Nicholas B. Bolus, Atlanta, GA (US); Hyeon Ki Jeong, Atlanta, GA (US); Daniel Whittingslow, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1042 days.

(21) Appl. No.: 17/126,300

(22) Filed: Dec. 18, 2020

(65) Prior Publication Data
US 2021/0137458 A1 May 13, 2021

Related U.S. Application Data

(63) Continuation-in-part of application No. 16/898,712, filed on Jun. 11, 2020, now abandoned.

(60) Provisional application No. 62/860,604, filed on Jun. 12, 2019.

(51) Int. Cl.
*A61B 5/00* (2006.01)
*A61B 5/053* (2021.01)
*A61B 7/00* (2006.01)
*A61B 7/04* (2006.01)

(52) U.S. Cl.
CPC .......... *A61B 5/6826* (2013.01); *A61B 5/0051* (2013.01); *A61B 5/053* (2013.01); *A61B 5/4528* (2013.01); *A61B 5/6806* (2013.01); *A61B 5/6843* (2013.01); *A61B 5/742* (2013.01);
(Continued)

(58) Field of Classification Search
CPC ..... A61B 5/6826; A61B 5/0051; A61B 5/053; A61B 5/4528; A61B 5/6806; A61B 5/6843; A61B 5/74–746; A61B 7/006; A61B 7/04; A61B 5/0002; A61B 2562/0219; A61B 2560/0418; A61B 5/0053; A61B 5/4585; A61B 5/7246; A61B 5/6828
See application file for complete search history.

(56) References Cited

U.S. PATENT DOCUMENTS 5,496,257 A * 3/1996 Kelly .................. A61H 31/005
                                                    601/134
6,537,233 B1   3/2003 Rangayyan et al.
6,930,608 B2   8/2005 Grajales et al.
(Continued)

OTHER PUBLICATIONS

Spain et al.: "Acoustic Monitoring of Joint Health"; Nov. 11, 2020 (no later than); Data Acquisition—Recent Advances and Applications in Biomedical Engineering; IntechOpen.
(Continued)

*Primary Examiner* — David J. McCrosky
(74) *Attorney, Agent, or Firm* — Bryan W. Bockhop; Bockhop Intellectual Property Law, LLC

(57) ABSTRACT

A bio-vibration device for use by a user having a finger for sensing vibration signals in an individual includes a finger coupler device, a vibration sensor and a communications circuit. The vibration sensor is affixed to the finger coupler device and is configured to be pressed against a selected site of the individual so as to sense a vibration signal therefrom. The communications circuit is responsive to the vibration sensor and is configured to transmit the vibration signal to a remote device.

27 Claims, 3 Drawing Sheets

(52) U.S. Cl.
CPC ............... *A61B 7/006* (2013.01); *A61B 7/04* (2013.01); *A61B 5/0002* (2013.01); *A61B 2562/0219* (2013.01)

(56) References Cited

U.S. PATENT DOCUMENTS

| | | | |
|---|---|---|---|
| 9,402,582 B1* | 8/2016 | Parviz | A61B 5/1455 |
| 10,420,387 B2* | 9/2019 | Zambriski | A61B 5/0024 |
| 10,585,534 B2 | 3/2020 | Tang et al. | |
| 11,857,297 B1* | 1/2024 | Williams | A61B 5/022 |
| 2006/0025690 A1 | 2/2006 | Guigne et al. | |
| 2010/0262047 A1 | 10/2010 | Genis | |
| 2011/0137210 A1* | 6/2011 | Johnson | A61B 5/021 |
| | | | 600/586 |
| 2012/0035509 A1* | 2/2012 | Wilson | A61B 5/1038 |
| | | | 600/592 |
| 2013/0211259 A1 | 8/2013 | Komistek et al. | |
| 2014/0128689 A1 | 5/2014 | Stewart et al. | |
| 2014/0275888 A1* | 9/2014 | Wegerich | A61B 5/053 |
| | | | 600/324 |
| 2015/0224021 A1 | 8/2015 | Centen et al. | |
| 2022/0133216 A1* | 5/2022 | Chen | A61B 5/447 |
| | | | 600/306 |
| 2022/0304890 A1* | 9/2022 | Kohler | A61H 31/007 |

OTHER PUBLICATIONS

Saggio et al.: "Wireless Sensory Glove System developed for advanced Human Computer Interface"; 2012; International Journal of Information Science; Scientific & Academic Publishing.
Wikipedia: "Power Glove"; Dec. 4, 2020.
Kalo et al.: "Reliability of Vibroarthography to Assess Knee Joint Sounds in Motion"; Apr. 2, 2020; Sensors; MDPI.
Jeong et al. "b-Value: A Potential Biomarker for Assessing Knee-Joint Health Using Acoustical Emission Sensing"; Dec. 1, 2019; IEEE Sesn Lett.
Sturman et al: "A Survey of Glove-based Input"; 1994; IEEE Computer Graphics & Applications.

* cited by examiner

GLOVE-BASED FORM FACTOR FOR BIO-ACOUSTICAL SENSING

CROSS-REFERENCE TO RELATED APPLICATION(S)

This application claims the benefit of U.S. Provisional Patent Application Ser. No. 62/860,604, filed Jun. 12, 2019, the entirety of which is hereby incorporated herein by reference.

This application is a continuation-in-part of, and claims the benefit of, U.S. patent application Ser. No. 16/898,712, filed Jun. 11, 2020, the entirety of which is hereby incorporated herein by reference.

STATEMENT OF GOVERNMENT SUPPORT

This invention was made with government support under grant number R01EB023808 awarded by the National Institutes of Health and under grant number 1749677 awarded by the National Science Foundation. The government has certain rights in the invention.

BACKGROUND OF THE INVENTION

Field of the Invention

The present invention relates to bio-sensor systems and, more specifically, to a bio-vibration sensor system.

Description of the Related Art

Injuries and chronic disorders affecting joints are pervasive and degrade quality of life for millions of individuals. The knee joint, due to its anatomical complexity, role in weight bearing, and high, cyclical exposure to mechanical stress, is particularly susceptible to injury. The current diagnostic standard for acute joint injury and chronic conditions such as osteoarthritis involves a combination of medical imaging, which can be costly and time-intensive, and physical examination, which often relies on subjective evaluations made on the part of either the clinician or the patient. Moreover, these methods are not ideally suited to longitudinal, comprehensive monitoring of joint health, which may benefit recovery.

Recent research has demonstrated the viability of using the acoustic emissions produced by joints in motion—in particular, the knee—as an indicator of underlying joint health. The concept of sensing skin vibrations (i.e., their local accelerations) caused by joint articulation is sometimes referred to as "vibroarthrography." These vibrations produce an acoustic response in the surrounding media, which is why the signal is often termed a "joint sound" or "acoustic emission." Arthro-acoustic techniques have been explored in both clinical and ambulatory settings, using both benchtop and wearable equipment. Results from these studies have demonstrated an ability to discriminate reliably between the acoustic signatures of healthy and impaired joints, and those of joints under varying mechanical load. One study explored the use of a vertical leg press as a reliable paradigm for modifying the acoustic output of a healthy knee, demonstrating a change in the heterogeneity of the joint sound as a function of percent body weight applied.

Current methods of sensing vibrations resulting from joint articulation typically involve taping or otherwise securing a vibration sensor (such as with an adhesive pad) to a selected site on the patient's skin (such as next to the patient's knee), instructing the patient to flex the joint and then sensing vibrations generated as a result of the flexing. Frequently, the sensor often has to be moved around several times until an optimal vibration signal is detected. However, such moving of the sensor can be difficult as the tape holding the sensor has to be peeled away from the patient's skin each time the sensor is moved. The peeling away of the tape is time consuming and can cause irritation to the patient's skin.

Also, the use of adhesive couplings between the sensor and the skin limit the amount of control over the force applied to the sensor. Insufficient force can result in an unnecessarily weak vibration signal being sense and excessive force can result in patient discomfort. Additionally, the presence of tape, adhesives or mechanical securing devices can introduce noise or distortion to the vibration signal.

Therefore, there is a need for a system and method of sensing bio-vibrations at multiple sites without having to tape a sensor to the skin.

Therefore, there is also a need for a system and method of sensing bio-vibrations in which the force applied to the sensor can be controlled easily.

SUMMARY OF THE INVENTION

The disadvantages of the prior art are overcome by the present invention which, in one aspect, is a bio-vibration device for use by a user having a finger for sensing vibration signals in an individual, which includes a finger coupler device, a vibration sensor and a communications circuit. The vibration sensor is affixed to the finger coupler device and is configured to be pressed against a selected site of the individual so as to sense a vibration signal therefrom. The communications circuit is responsive to the vibration sensor and is configured to transmit the vibration signal to a remote device.

In another aspect, the invention is a bio-vibration device for sensing vibration signals in an individual that includes a hand-held device having a sensor end. A vibration sensor is affixed to the sensor end of the hand-held device and is configured to be pressed against a selected site of the individual and to sense a vibration signal therefrom. A communications circuit is responsive to the vibration sensor and is configured to transmit the vibration signal to a remote device.

In yet another aspect, the invention is a method of retrieving information about an individual, in which a vibration sensor device is secured to a user's finger. The finger is used to press the vibration sensor against a selected site on the individual with a force applied within a predetermined range. Information from the vibration sensor is transmitted to a remote device.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
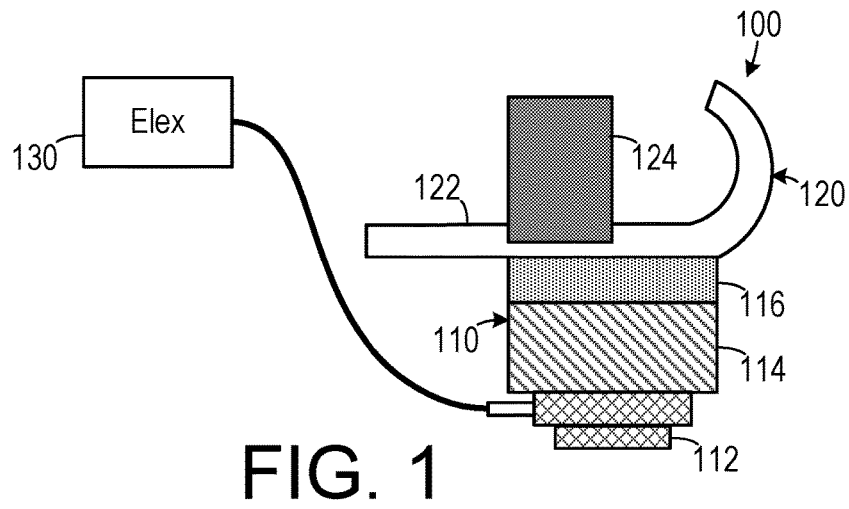
FIG. 1 is a schematic diagram of one embodiment of a bio-vibrational sensor.

A preferred embodiment of the invention is now described in detail. Referring to the drawings, like numbers indicate like parts throughout the views. Unless otherwise specifically indicated in the disclosure that follows, the drawings are not necessarily drawn to scale. The present disclosure should in no way be limited to the exemplary implementations and techniques illustrated in the drawings and described below. As used in the description herein and throughout the claims, the following terms take the meanings explicitly associated herein, unless the context clearly dictates otherwise: the meaning of "a," "an," and "the" includes plural reference, the meaning of "in" includes "in" and "on."

Also, as used herein "bio-vibration" and "vibration" include any type of mechanical vibration generated by a biological system, including acoustic vibrations, infra-acoustic vibrations and ultra-acoustic vibrations.

One representative embodiment of the invention employs alternative form factors for collecting joint sounds that would improve the quality and reliability of the measurements and eliminate the need for consumables like tape and adhesive microphone pads. Such form factors include contact microphones that can be affixed to a finger-attachable frame or that are embedded in a glove. The sensor can then be placed at locations of interest around a joint to collect arthro-acoustic data. This approach offers several advantages, including the ability to finely regulate contact pressure at the sensor-to-skin interface (by leveraging the user's inherent motor control and tactile feedback mechanisms) while eliminating interface noise caused by adhesive, fabric, or other material interacting with the skin. Additionally, an adhesive-based solution is not ideally suited to applications involving repeated use, such as longitudinal tracking in a home setting. The hand-worn or hand-held systems of the present invention can be easily and repeatedly administered. Furthermore, they can provide an opportunity for an individual to engage actively in the management of one's own or a dependent's care. For example, a parent might use the present invention to collect joint acoustic data on a child suffering from juvenile idiopathic arthritis.

Figure 2:
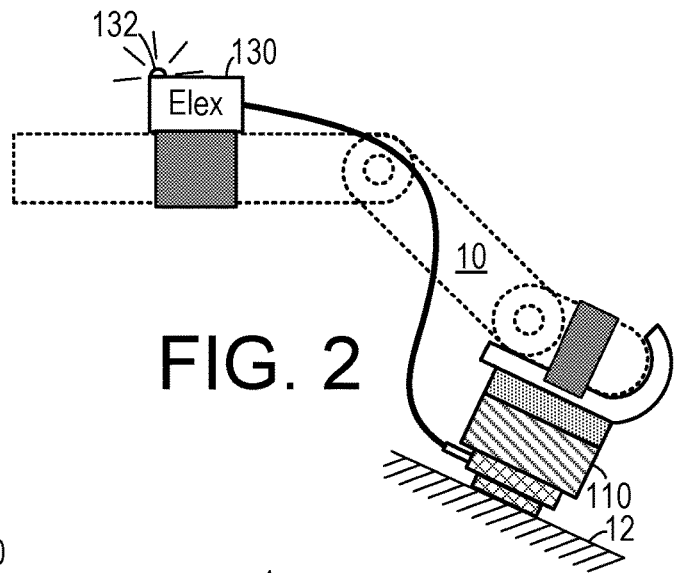
FIG. 2 is a schematic diagram of the embodiment shown in FIG. 1 applied to a finger.

As shown in FIGS. 1 and 2, one embodiment of a bio-vibrational sensing system 100 includes a finger coupler device 120, which can include a frame 122 and a mechanism 124 for securing the frame 122 to a user's finger 10. (The user can be, for example, a physician, a physical therapist, a technician, or even an individual trained to use the device—such as a coach, a parent or even the patient.) A sensor unit 110 is affixed to the frame 122 and includes a bio-vibration sensor 112, which could include a miniature, high-bandwidth, uniaxial accelerometer (e.g., with a sensitivity of 100 mV/g, a frequency response of ±10%=2 to 10,000 Hz; and which in one experimental embodiment includes a Series 3225 accelerometer available from Dytran Instruments, Inc., Chatsworth, CA, USA). The bio-vibration sensor 112 can also include a microphone in certain embodiments. The bio-vibration sensor 112 should be sensitive enough to resolve small vibrations caused by the articulation of the internal components of the knee joint that travel to the skin surface.

A force sensor 116, such as a capacitive force sensor (e.g., a CS8-10N, available from SingleTact, Los Angeles, CA, US encased in silicone rubber, e.g., OOMOO 30, available from Smooth-On, Lower Macungie, PA, USA) is sandwiched between the bio-vibration sensor 112 and the frame 122. A rigid plastic housing 114 can be used to couple the bio-vibration sensor 112 to the force sensor 116. In one embodiment, the force sensor 116 has a full-scale sensing range of 0 N to 10 N). The force sensor 116 measures contact pressure between the bio-vibration sensor 112 and the individual's skin 12. Such a force measurement complements the acoustic signal captured by the bio-vibration sensor 112, providing context such as whether inconsistent contact is made, which can be a source of signal artifact. Also, the force measurement can help the user gauge the quality of the joint sound recording. Additionally, the contact force measurement, in conjunction with real-time sensory (e.g., visual, haptic) feedback, can be used as a mechanism for training users to apply consistent pressure at the sensor-to-skin interface, reducing inter-trial and inter-user variability of recordings. A capacitive force sensor by itself can be delicate and prone to delamination, so using a silicone rubber envelope can protect the force sensor 116 from damage while still allowing it to deflect and measure force.

A multi-color LED 132 can provide visual feedback of sensor contact force via a force-indicating color scheme. For example, a green light can indicate that the user is pressing within a desired range of contact force for consistent signal acquisition, a blue light can indicate that insufficient force is being used to acquire an optimal signal and a red light can indicate that force above a desired range is being employed. This feedback mechanism can help to ensure that consistent contact pressure is maintained across trials and across subjects. In one experimental embodiment, intermediate values of contact force (roughly between 4 N and 7 N) were found to produce repeatable results in terms of root-mean-squared (RMS) amplitude in the frequency band of interest, while pressing too hard (between 8 and 10 N) led to discomfort in some subjects. In certain embodiments, force feedback can employ other indicators, such as a sonic force feedback indicator.

Figure 3:
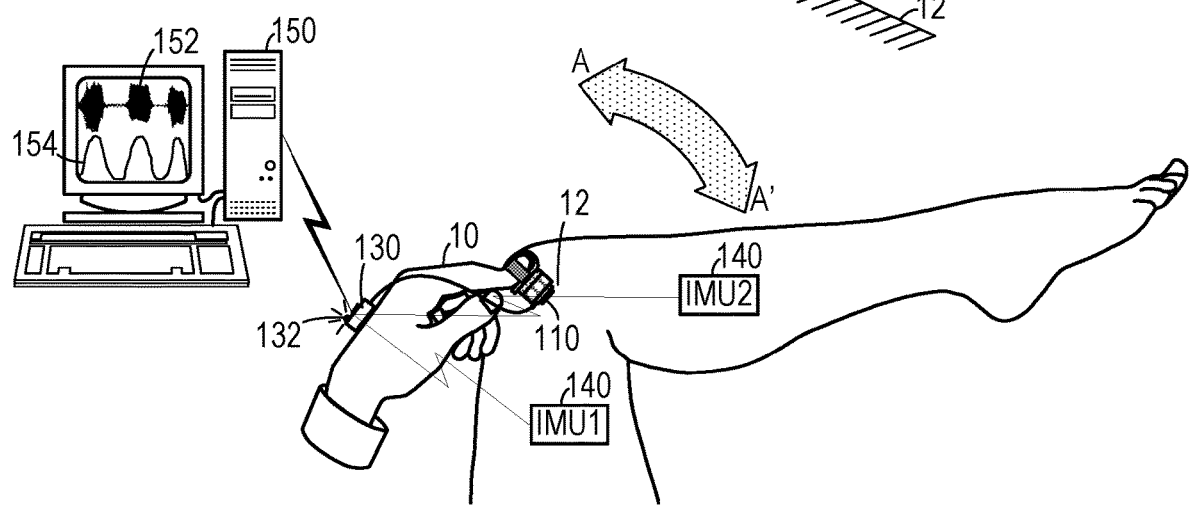
FIG. 3 is a schematic diagram of a multi-modal joint sensing system.

As shown in FIG. 3, a communications and control circuit 130 is responsive to the bio-vibration sensor 112 and transmits the vibration signal received from the bio-vibration sensor 112 to a remote device 150, such as a computer. Communication with the remote device 150 can be either wirelessly or hard-wired. Joint position and movement sensors 140 (such as accelerometers that communicate with the communications and control circuit 130 either wirelessly or using hard wired channels) can be applied to the areas around the joint and indicate the relative positions of the joint members (i.e., the flexure angle of the joint). In one experimental embodiment, two inertial measurement units 140 (IMUs) (BNO055 available from Bosch Sensortec, Reutlingen, Germany)—one for the leg shank segment and one for the thigh segment—were employed. These ensured consistent knee joint displacement and velocity, which can affect the acoustic output of the joint, across repetitions of a leg press. These quaternions were used to estimate the knee joint angle across the leg press maneuver.

In use, the user 10 applies the sensor unit 110 to a selected site 112 on the patient's skin (typically near the joint of interest) and instructs the patient to flex the joint (e.g., along directions A-A'). The bio-vibration sensor 112 senses vibrations produced by the joint during flexing, the inertial measurement units 140 indicate the joint flexure and the communications and control circuit 130 transmits the resulting sensed signal to the remote unit 150, which can employ known digital signal processing and artificial intelligence techniques to provide useful information about the joint. Also, the remote unit 150 can display a graphical representation of both the flexing angle 154 and the resulting vibrational signal 152 on a video display. This video display can be used to ensure that the movement of the joint occurs at a consistent speed across several repetitions.

Figure 4:
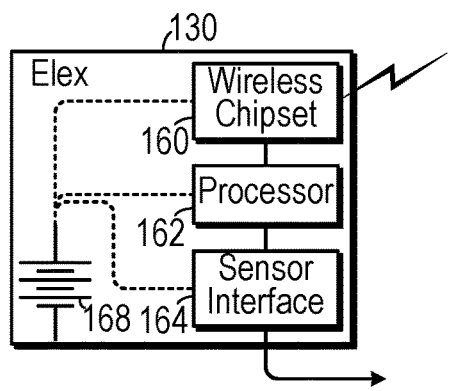
FIG. 4 is a schematic diagram of a communications and control circuit employed in one embodiment of a joint sensing system.

As shown in FIG. 4, the communications and control circuit 130 can include a power supply 168, such as a battery. A sensor interface 164 receives input from the sensors and a processor 162 provides feedback from the force sensor and transforms the received signals as necessary. A wireless chipset 160 (e.g. a BlueTooth chipset, a Zigbee chipset, a cellular chipset, etc., depending upon the specific application) transmits the signals to the remote device. In certain embodiments, the communications and control circuit 130 can be hard wired to the remote device.

Figures 5A, 5B:
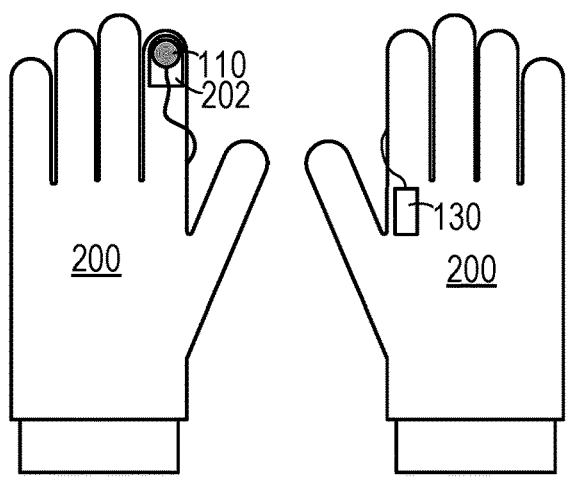
FIG. 5A is a palm-side view of a glove-based bio-vibrational sensor system.
FIG. 5B is a back-side view of the glove-based system shown in FIG. 5A.

As shown in FIGS. 5A and 5B, a glove-based arthroacoustic sensing system includes a glove 200 to which various sensing and data acquisition components 202 are mounted. One experimental embodiment used a latex/neoprene cleaning glove (available from Playtex, Dover, DE, USA). Such a glove it is easy to disinfect and has an elasticity that enables a solid, contoured fit to the user's digits.

Figure 6A:
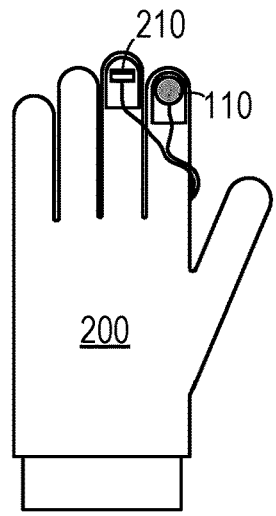
FIG. 6A is a schematic diagram of a multi-modal joint sensor system.
Figure 6B:
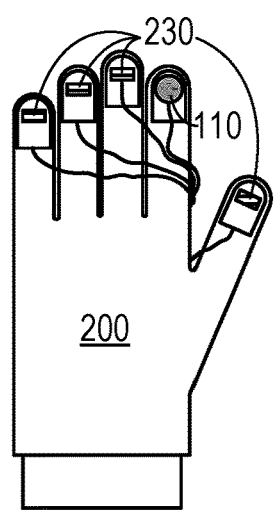
FIG. 6B is a schematic diagram of a multi-modal joint sensor system employing a plurality of electrodes.

As shown in FIG. 6A, additional types of sensors 210 may be employed. For example, a finger-mounted transducer can be used to generate an applied vibration signal that is applied to the selected site and the vibration sensor can be configured to sense reflections of the applied vibration signal. Also, a pair of electrodes can be used to determine impedance of the tissues (e.g., subcutaneous tissues) at the site of interest. The communications and control and a circuit can then generate information regarding impedance of tissues of individual at the site, which can be indicative of localized swelling at the site. In a multi-modal sensing system, the processor can be configured to analyze the vibration signal, the movement signal, the force applied by the user and the impedance information so as to generate an output indicative of a state of the joint. One embodiment, as shown in FIG. 6B, employs a set of four electrodes 230 used to measure impedance in the tissues.

In one experimental embodiment, data from the capacitive force sensor and both IMUS were collected by a Teensy 3.6 microcontroller (PJRC available from Sherwood, OR, USA) at a sampling rate of 100 Hz and logged on a microSD card. The microcontroller was housed in a custom enclosure, along with a Bluetooth module (SPBT3.0DP1 available form STMicroelectronics, Geneva, Switzerland) for streaming data to a laptop computer and sending/receiving a start/stop signal from MATLAB (MathWorks, Natick, MA, USA). A National Instruments data acquisition unit (USB-4432, Austin, TX, USA) was used to collect the acoustic signals from the four accelerometers at 50 kHz per channel. The key result is shown in FIG. 7, which shows that relative grinding loudness (RMS of the low-pass-filtered joint sound signal, referenced to the no-load, or 0% BW, condition) within the knee increased significantly ($p<0.01$, using paired sample t-test with Holm-Bonferroni correction) and monotonically with vertical loading for all three mounting techniques across subjects.

Figure 7:
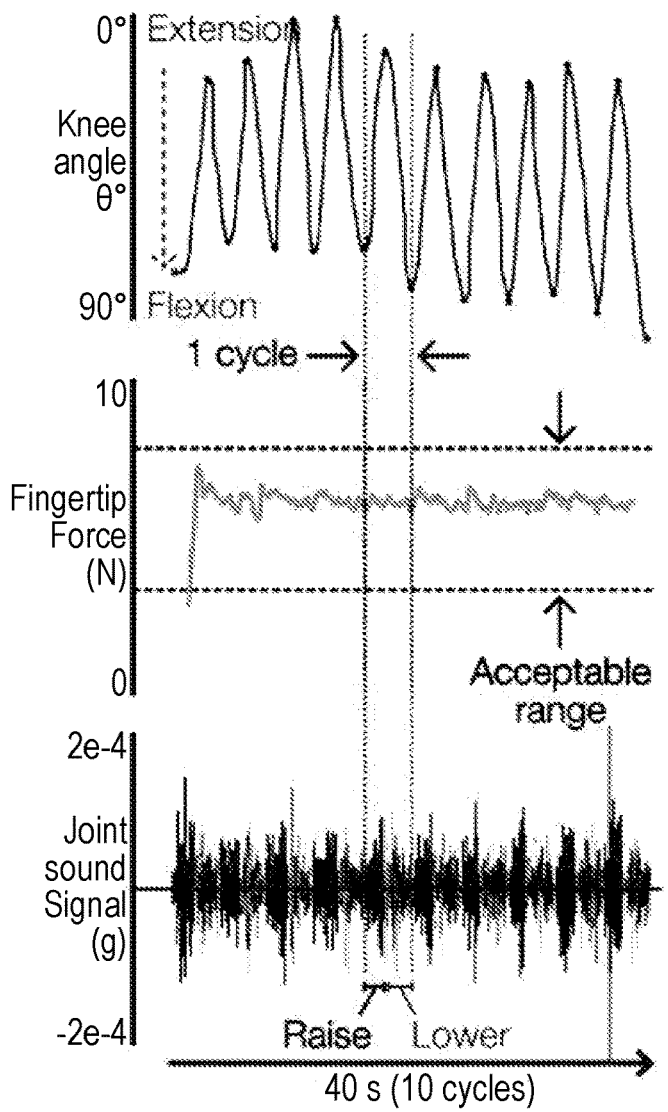
FIG. 7 is a chart relating joint extension, fingertip force to a joint bio-vibrational signal.

Sample time-series waveforms of signals collected by the glove system during a single experiment trial, consisting of 10 vertical leg press cycles is shown in FIG. 7. IMUs were used to confirm that consistent knee range of motion (in degrees, °) was achieved at a constant cadence and to segment the joint sound signal into individual cycles. Contact force (in N) at the fingertip was measured to confirm a consistent amount of pressure was applied. The joint sound signal (local acceleration, in g) was captured by a fingertip-mounted vibration sensor and segmented into cycles consisting of extension ("raise") and flexion ("lower") phases.

Figure 8:
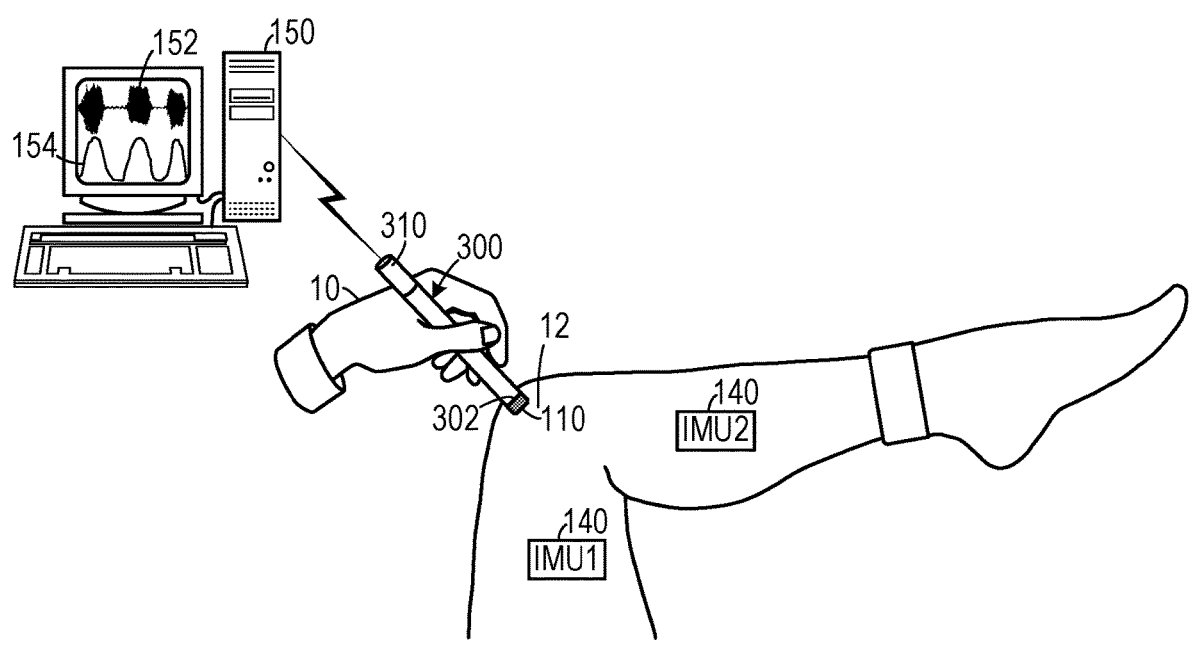
FIG. 8 is a schematic diagram of a hand-held joint bio-vibration sensor system.

As shown in FIG. 8, one embodiment can include a hand-held device 300 having a sensor end 302 to which the bio-vibration sensor 110 is affixed. The communications and control circuit 310 can be integrated in the hand-held device 300.

Although specific advantages have been enumerated above, various embodiments may include some, none, or all of the enumerated advantages. Other technical advantages may become readily apparent to one of ordinary skill in the art after review of the following figures and description. It is understood that, although exemplary embodiments are illustrated in the figures and described below, the principles of the present disclosure may be implemented using any number of techniques, whether currently known or not. Modifications, additions, or omissions may be made to the systems, apparatuses, and methods described herein without departing from the scope of the invention. The components of the systems and apparatuses may be integrated or separated. The operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. It is intended that the claims and claim elements recited below do not invoke 35 U.S.C. § 112(f) unless the words "means for" or "step for" are explicitly used in the particular claim. The above-described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A bio-vibration device for use by a user, having a hand with a back side and a finger, for sensing vibration signals in an individual, comprising:
    (a) a finger coupler device;
    (b) a vibration sensor affixed to the finger coupler device and configured to be pressed against a selected site of the individual and to sense a vibration signal therefrom;
    (c) a communications circuit that is responsive to the vibration sensor and that is configured to transmit the vibration signal to a remote device;

(d) a force sensor disposed between the vibration sensor and the finger coupler device that senses a force applied to the selected site by the user; and (e) a force feedback circuit that is responsive to the force sensor and that determines if the force sensed by the force sensor is within a desired range for consistent signal acquisition by the vibration sensor, the force feedback circuit including a multi-color LED, configured to be disposed on the back side of the hand, that generates: light of a first color when the force applied by the user is within the desired range; light of a second color, different from the first color, when the force applied by the user is below the desired range; and light of a third color, different from the first color and the second color, when the force applied by the user is above the desired range so as to provide visual feedback of sensor contact force.

2. The bio-vibration device of claim 1, wherein the communications circuit comprises a wireless chipset.

3. The bio-vibration device of claim 1, wherein the force sensor comprises a capacitance-based film sensor.

4. The bio-vibration device of claim 1, wherein the selected site includes are area around a joint of the user and wherein the remote device comprises a processor that is configured to analyze the vibration signal and to generate an output indicative of a state of the joint.

5. The bio-vibration device of claim 4, further comprising at least one movement sensor that is configured to be applied to a part of the individual near the joint and configured to generate a movement signal indicating movement in the joint.

6. The bio-vibration device of claim 5, wherein the vibration sensor comprises a selected one of an accelerometer and a microphone.

7. The bio-vibration device of claim 1, wherein the finger coupler device includes a glove including at least one fingertip covering to which the vibration sensor is affixed.

8. The bio-vibration device of claim 1, further comprising a finger-mounted transducer for generating an applied vibration signal that is applied to the selected site and wherein the vibration sensor is configured to sense reflections of the applied vibration signal.

9. The bio-vibration device of claim 1, further comprising a set of four electrodes and a circuit that generates information regarding impedance of tissues of individual at the site and wherein the wireless communications circuit that is responsive to the electrodes and is configured to transmit the impedance information to a remote device.

10. The bio-vibration sensor of claim 1, wherein the selected site includes an area around a joint of the user, the sensor configured as a multi-modal sensing system and further comprising:

(a) at least one movement sensor that is configured to be applied to a part of the individual near the joint and configured to generate a movement signal indicating movement in the joint;

(b) a force sensor configured to sense a force applied to the selected site by the user;

(c b) a set of four electrodes and a circuit that generates information regarding impedance of the tissues of individual at the site; and (d c) a processor that is configured to analyze the vibration signal, the movement signal, the force applied by the user and the impedance information so as to generate an output indicative of a state of the joint.

11. A bio-vibration device for use by a user, having a hand with a back side and a finger, for sensing vibration signals in an individual, comprising:

(a) a finger coupler device;

(b) a vibration sensor affixed to the finger coupler device and configured to be pressed against a selected site of the individual and to sense a vibration signal therefrom; and (c) a communications circuit that is responsive to the vibration sensor and that is configured to transmit the vibration signal to a remote device;

(d) a force sensor disposed between the vibration sensor and the finger coupler device that senses a force applied to the selected site by the user; and (e) a force feedback circuit that is responsive to the force sensor and that determines if the force sensed by the force sensor is within a desired range, the force feedback circuit including a multi-color LED, configured to be disposed on the back side of the hand, that generates: light of a first color when the force applied by the user is between 4N and 7N; light of a second color, different from the first color, when the first color and the second color, when the force applied by the user is above 7N so as to provide visual feedback of sensor contact force.

12. The bio-vibration device of claim 11, wherein the communications circuit comprises a wireless chipset.

13. The bio-vibration device of claim 11, wherein the force sensor comprises a capacitance-based film sensor.

14. The bio-vibration device of claim 11, wherein the selected site includes an area around a joint of the user and wherein the remote device comprises a processor that is configured to analyze the vibration signal and to generate an output indicative of a state of the joint.

15. The bio-vibration device of claim 14, further comprising at least one movement sensor that is configured to be applied to a part of the individual near the joint and configured to generate a movement signal indicating movement in the joint.

16. The bio-vibration device of claim 15, wherein the vibration sensor comprises a selected one of an accelerometer and a microphone.

17. The bio-vibration device of claim 11, wherein the finger coupler device includes a glove including at least one fingertip covering to which the vibration sensor is affixed.

18. The bio-vibration device of claim 11, further comprising a finger-mounted transducer for generating an applied vibration signal that is applied to the selected site and wherein the vibration sensor is configured to sense reflections of the applied vibration signal.

19. The bio-vibration device of claim 11, further comprising a set of four electrodes and a circuit that generated information regarding impedance of tissues of individual at the site and wherein the wireless communications circuit that is responsive to the electrodes and is configured to transmit the impedance information to a remote device.

20. The bio-vibration device of claim 11, wherein the selected site includes an area around a joint of the user, the sensor configured as a multi-modal sensing system and further comprising:

(a) at least one movement sensor that is configured to be applied to a part of the individual near the joint and configured to generate a movement signal indicating movement in the joint;

(b) a set of four electrodes and a circuit that generates information regarding impedance of the tissues of individual at the site; and (c) a processor that is configured to analyze the vibration signal, the movement signal, the force applied by the user and the impedance information so as to generate an output indicative of a state of the joint.

21. A bio-vibration device for use by a user, having a hand and a finger, for sensing vibration signals in an individual, comprising:
(a) a finger coupler device;
(b) a vibration sensor affixed to the finger coupler device and configured to be pressed against a selected site of the individual and to sense a vibration signal therefrom; and
(c) a communications circuit that is responsive to the vibration sensor and that is configured to transmit the vibration signal to a remote device;
(f) a force sensor disposed between the vibration sensor and the finger coupler device that senses a force applied to the selected site by the user;
(g) a force feedback circuit that is responsive to the force sensor and that determines if the force sensed by the force sensor is within a desired range for consistent signal acquisition, the force feedback circuit including an indicator that generates: a first user-perceptible indicator when the force applied by the user is within the desired range; a second user-perceptible indicator different from the first user-perceptible indicator when the force applied by the user is below the desired range; and third user-perceptible indicator, different from the first user-perceptible indicator and the second user-perceptible indicator, when the force applied by the user is above desired range so as to provide feedback of sensor contact force as the vibration sensor is being applied to the selected site;
(h) a first inertial measurement unit that is applied to a first part of the individual near the joint and a second inertial measurement unit that is applied to a second part of the individual near the joint, spaced apart from the first part of the individual and positioned so as to measure flexure angle of the joint; and
(i) a video display that displays a graphical representation of both a flexing angle of the joint and the vibrational signal.

22. The bio-vibration device of claim 21, wherein the communications circuit comprises a wireless chipset.

23. The bio-vibration device of claim 21, wherein the force sensor comprises a capacitance-based film sensor.

24. The bio-vibration device of claim 21, wherein the selected site includes an area around a joint of the user and wherein the remote device comprises a processor that is configured to analyze the vibration signal and to generate an output indicative of a state of the joint.

25. The bio-vibration device of claim 21, wherein the finger coupler device includes a glove including at least one fingertip covering to which the vibration sensor is affixed.

26. The bio-vibration device of claim 21, further comprising a finger-mounted transducer for generating an applied vibration signal that is applied to the selected site and wherein the vibration sensor is configured to sense reflections of the applied vibration signal.

27. The bio-vibration device of claim 21, further comprising a set of four electrodes and a circuit that generates information regarding impedance of tissues of individual at the site and wherein the wireless communications circuit that is responsive to the electrodes and is configured to transmit the impedance information to a remote device.

* * * * *